United States Patent [19]

Fenoglio

[11] 4,212,992

[45] Jul. 15, 1980

[54] FIRE RETARDANTS

[75] Inventor: David J. Fenoglio, Carol Stream, Ill.

[73] Assignee: Standard Oil Company (Indiana), Chicago, Ill.

[21] Appl. No.: 751,133

[22] Filed: Dec. 16, 1976

Related U.S. Application Data

[62] Division of Ser. No. 434,347, Jan. 17, 1974, Pat. No. 4,041,016.

[51] Int. Cl.$^2$ .................. C07C 63/44; C07C 49/44
[52] U.S. Cl. .................. 562/492; 260/649 R; 568/633; 568/328
[58] Field of Search .......... 260/648 C, 649 R, 590 B; 568/633; 562/492

[56] References Cited

U.S. PATENT DOCUMENTS

| | | | |
|---|---|---|---|
| 3,642,923 | 2/1972 | Foster et al. | 260/648 C |
| 3,859,371 | 1/1975 | Ilardo | 260/648 C |
| 3,884,970 | 5/1975 | Arakawa et al. | 260/648 C |

*Primary Examiner*—C. Davis
*Attorney, Agent, or Firm*—William H. Magidson; William T. McClain

[57] ABSTRACT

Fire retardant adducts of 1,4-dihydronaphthalene and halocyclopentadienes and polymer compositions containing said adducts.

6 Claims, No Drawings

FIRE RETARDANTS

This is a division of a application Ser. No. 434,347 filed Jan. 17, 1974 now U.S. Pat. No. 4,041,016.

This invention relates to adducts of 1,4-dihydronaphthalene and halocyclopentadienes and fire retardant composition comprising polyolefins and adducts of 1,4-dihydronaphthalene and halocyclopentadienes.

There has been considerable interest in the development of fire-retardant compositions, particularly polyolefin compositions having improved fire-retardancy.

The general object of this invention is to provide a new class of compounds suitable for use as fire-retardants. Another object of this invention is to provide polyolefin compositions having improved fire-retardancy. Other objects appear hereinafter.

I have now found that adducts of 1,4-dihydronaphthalene and halocyclopentadienes and modifications of said adducts constitute a new class of fire-retardants, which are compatible with polyolefins and improve the fire-retardancy of these compositions. Compounds capable of improving the fire-retardancy of polyolefins include 1,2,3,4-tetrahalonaphthobornadienes, such as 1,2,3,4-tetrachloronaphthobornadiene, 1,2,3,4-tetrabromonaphthobornadiene; 1,2,3,4,7,7-hexahalonaphthobornadienes; 1,2,3,4-tetrachloro-7,7-dialkoxy (methoxy, ethoxy,propoxy)-naphthobornadienes; 1,2,3,4-tetrahalo-7-one-naphthobornadienes, etc. 2,3,4-trichloro-9,10; 4a,9a-tetrahydroanthracene-1-carboxylic acid, etc.

Briefly, most of these compounds can be produced by reacting 1,4-dihydronaphthalene and a suitable halosubstituted cyclopentadiene. While all of these adducts can be used directly in polyolefin compositions or converted to other compounds, the 7,7-dialkoxy compounds can be converted to 7-ones which in turn can be converted to tetrahydroanthracene-1 carboxylic acids as explained below.

In somewhat greater detail, 1,4-dihydronaphthalene and a suitable halosubstituted cyclopentadiene, such as a hexahalocyclopentadiene (hexachlorocyclopentadiene, hexabromocyclopentadiene, etc.), 5,5-dialkoxy-1,2,3,4-tetrachlorocyclopentadiene (5,5-dimethoxy-1,2,3,4-tetrabromopentadiene, 5,5-diisopropoxy-1,2,3,4-tetrachloropentadiene, etc.) 1,2,3,4-tetrahalocyclopentadiene, (1,2,3,4-tetrabromocyclopentadiene) etc. is heated to a temperature of 100° to 150° C. to form a Diels-Alder adduct. The reaction can be carried out in a solvent, such as tetrachloroethylene or without a solvent under atmospheric conditions or in an autoclave under pressure, such as autogeneous pressure.

The 7,7-dialkoxy groups can be converted to keto groups (7-ones) by treating the adducts with a dehydrating acid, such as sulfuric acid at 30° to 40° C., preferably under ambient conditions. The reaction can be carried out in a halohydrocarbon solvent, such as methylene dichloride, 1,1,1-trichloroethane, etc.

The 1,2,3,4-tetrahalo-7-one-naphthobornadienes can be converted to 2,3,4-trihalo-9,10; 4a,9a-tetrahydroanthracene-1-carboxylic acids by reacting the 1,2,3,4-tetrahalo-7-one-naphthobornadienes with a suspension of powdered alkali metal hydroxide, such as powdered sodium hydroxide or potassium hydroxide in an aprotic solvent, such as tetrahydrofuran, at 0° to 5° C.

All of the aforesaid halo compounds can be added to polyolefin compositions in a concentration of about 5 to 50 parts by weight per 100 parts by weight polyolefin to improve the fire-retardant properties of the polyolefin composition. For the purpose of this invention the term "polyolefin" includes solid polymers which contain a major proportion (i.e., greater than 50% and generally greater than 75%) of an aliphatic olefin, having from 2 to 8 carbon atoms, such as polyethylene, substantially crystalline polypropylene, propylene-ethylene block or random copolymers, ethylene-butene-1 block or random copolymers, polybutene-1, poly(4-methylpentene-1), poly(3-methyl-butene-1), and the like. The term polyolefin as used herein is, furthermore, intended to include copolymers of hydrocarbon monomers with copolymerizable polar monomers with such functional monomers constituting a minor proportion of the copolymer. Preferred polyolefins are polypropylene and propylene-ethylene copolymers such as propylene-ethylene terminal block and multisegment copolymers. Propylene-ethylene multisegment copolymers are described in U.S. Pat. Nos. 3,296,338 and 3,442,978.

The polyolefin composition can be compounded with various inoccuous additives, such as inert fillers (fiber glass, zinc oxide, etc.) or other fire retardant agents such as phosphorous compounds (triphenyl phosphite), filler (antimony trioxide), etc. The fire retardants lower the level of the new additive of this invention necessary to impart a particular level of fire retardancy.

Although all the adducts of this invention can be used in fire retardant polyolefin composition, various compounds have additional uses. For example, 2,3,4-trichloro-9,10; 4a,9a-tetrahydroanthracene-1-carboxylic acid shows severe necrosis to pigweed and moderate retardation against yellow foxtail weed while 1,2,3,4-tetrachloro-7-one-naphthobornadiene shows 51% control of late blight of tomatoes with no damage to the plants, 80% control of powdery mildew of cucumber with no damage to the plants and 72% control of bacterial leaf spot of tomatoes.

The following examples are merely illustrative.

EXAMPLE I

Thirteen grams 1,4-dihydronaphthalene (0.1 mole) and 27.3 grams hexachlorocyclopentadiene (0.1 mole) were heated at 130° to 140° C. for 48 hours in a 100 ml 3-necked round bottomed flask equipped with a condenser, thermometer, heating mantle and magnetic stirrer. The dark reddish-brown liquid solidified on cooling yielding 38.2 grams (94.7% yield) of 1,2,3,4,7,7-hexachloronaphthobornadiene. White coulombic crystals melting at 139°–140° C. were obtained after recrystallization from methanol. The nmr and ir were consistent with the indicated structure and the chemical analysis for 1,2,3,4,7,7-hexachloronaphthobornadiene was as follows:

|  | Theory | Actual |
| --- | --- | --- |
| Carbon | 44.31 | 44.75 |
| Hydrogen | 2.50 | 2.46 |
| Chlorine | 52.79 | 52.90 |

The corresponding (a) 1,2,3,4,7,7-hexabromonaphthobornadiene, (b) 1,2,3,4-tetrachloronaphthobornadiene and (c) 1,2,3,4-tetrabromonaphthobornadiene can be obtained by replacing the hexachloropentadiene with an equal molar concentration of (a) hexabromopentadiene, (b) tetrachloropentadiene or (c) tetrabromopentadiene.

EXAMPLE II

One hundred thirty grams 1,4-dihydronaphthalene (1 mole) and 264 grams 1,1-dimethoxy-2,3,4,5-tetrachlorocyclopentadiene (1 mole) were heated at 140° to 145° C. for 48 hours in a 500 ml 3-necked flask equipped with a condenser, thermometer, heating mantle and magnetic stirrer. The hot liquid was poured into excess methanol yielding 290.77 grams (75.5% yield) of white solid 1,2,3,4-tetrachloro-7,7-dimethoxynaphthobornadiene. White coulombic crystals melting at 106° to 107° C. were obtained after recrystallization from methanol. The nmr, ir and chemical analysis were all consistent with the structure for 1,2,3,4-tetrachloro-7,7-dimethoxynaphthobornadiene.

The corresponding (a) 1,2,3,4-tetrabromo-7,7-dimethoxynaphthobornadiene, (b) 1,2,3,4-tetrachloro-7,7-diisopropoxynaphthobornadiene can be obtained by replacing the 1,1-dimethoxy-2,3,4,5-tetrachlorocyclopentadiene with an equal molar concentration of (a) 1,1-dimethoxy-2,3,4,5-tetrabromocyclopentadiene or (b) 1,1-diisopropoxy-2,3,4,5-tetrachlorocyclopentadiene.

EXAMPLE III

Fifty-eight grams 1,2,3,4-tetrachloro-7,7-dimethoxynaphthobornadiene (0.147 mole), 2,000 ml methylene dichloride and 1,250 ml concentrated sulfuric acid were stirred for three hours at room temperature in a 5 liter round bottomed flask during which time the reactants changed from a clear fluid to a viscous golden color. The methylene dichloride layer was separated and the acid layer extracted three times with 300 ml portions of methylene dichloride. The methylene dichloride portions were combined, washed with water, dried under anhydrous sodium sulfate, filtered and the solvent distilled off yielding 44.4 grams (87% yield) of tan-white 1,2,3,4-tetrachloro-7-one-naphthobornadiene. Clear coulombic crystals melting at 188°–189° C. were obtained after recrystallization from carbon tetrachloride. The nmr and ir were consistent with the structure for 1,2,3,4-tetrachloro-7-one-naphthobornadiene.

The corresponding 1,2,3,4-tetrabromo-7-one-naphthobornadiene can be obtained by replacing 1,2,3,4-tetrachloro-7,7-dimethoxynaphthobornadiene with an equal molar concentration of 1,2,3,4-tetrabromo-7,7-dimethoxynaphthobornadiene.

EXAMPLE IV

Eight and nine-tenths grams 1,2,3,4-tetrachloro-7-one naphthobornadiene (0.0256 mole) and 100 ml tetrahydrofuran were stirred at 0° C. in a 100 ml round necked flask equipped with a drying tube and a magnetic stirrer. After 8.25 grams of powdered sodium hydroxide was added, the reactants were stirred at 0° C. for 5 hours. Twenty ml 3.7 N hydrochloric acid was added to the reactants while maintaining at 0° C. followed by 25 ml water. The tetrahydrofuran was then removed using a rotar-evaporator. The residue was dissolved in 100 ml ethyl ether, washed with water, 100 ml 5% by weight aqueous sodium bicarbonate added followed by 15 ml 3.7 N hydrochloric acid forming a precipitate. The precipitate was dissolved in ethyl ether, washed with saturated aqueous sodium chloride and dried under anhydrous sodium sulfate. The ethyl ether was removed with a vacuum yielding 5.1 grams (60% yield) of 2,3,4-trichloro-9,10; 4a,9a-tetrahydroanthracene-1-carboxylic acid. White needle-like crystals melting at 209°–212° C. were obtained after recrystallization from ethylene dichloride. The nmr, ir and chemical analysis were consistent with the structure for 2,3,4-trichloro-9,10; 4a,9a-tetrahydroanthracene-1-carboxylic acid.

The corresponding 2,3,4-tribromo-9,10; 4a,9a-tetrahydroanthracene-1-carboxylic acid can be obtained by replacing 1,2,3,4-tetrachloro-7-one-naphthobornadiene with an equal molar concentration of 1,2,3,4-tetrabromo-7-one-naphthobornadiene.

EXAMPLE V

One hundred parts by weight crystalline polypropylene having a molecular weight of at least 2,000,000 was blended with 10 parts by weight antimony oxide and either 10 or 25 parts by weight of fire retardant compound of this invention, pelleted on an extruder having a die temperature of 425° F. and molded at 380° F. into bars 10 mm long, 3 mm thick and 6½ mm wide. The fire retardancy of the samples was evaluated according to ASTM D-2863-70. The results are set forth below in Table I.

Table I

| Compound Evaluated | Parts by Weight | Oxygen Index |
|---|---|---|
| Pure Polypropylene |  | 18.5 |
| 1,2,3,4,7,7-hexachloronaphthobornadiene | 10 | 22.1 |
| 1,2,3,4,7,7-hexachloronaphthobornadiene | 25 | 24.3 |
| 1,2,3,4-tetrachloro-7,7-dimethoxynaphthobornadiene | 10 | 20.9 |
| 1,2,3,4-tetrachloro-7,7-dimethoxynaphthobornadiene | 25 | 22.9 |
| 1,2,3,4-tetrachloro-7-one-naphthobornadiene | 10 | 21.1 |
| 1,2,3,4-tetrachloro-7-one-naphthobornadiene | 25 | 22.9 |

I claim:

1. A halogen containing compound selected from the group consisting of 1,2,3,4-tetrahalonaphthobornadienes, 1,2,3,4,7,7-hexahalonaphthobornadienes, 1,2,3,4-tetrahalo-7,7-dialkoxynaphthobornadienes, 1,2,3,4-tetrahalo-7-one-naphthobornadiene and 2,3,4-trihalo-9,10; 4a,9a-tetrahydroanthracene-1-carboxylic acid.

2. A halogen containing compound of claim 1, wherein said compound is 1,2,3,4-tetrachloronaphthobornadiene.

3. A halogen containing compound of claim 1, wherein said compound is 1,2,3,4,7,7-hexachloronaphthobornadiene.

4. A halogen containing compound of claim 1, wherein said compound is 1,2,3,4-tetrachloro-7,7-dimethoxy-naphthobornadiene.

5. A halogen containing compound of claim 1, wherein said compound is 1,2,3,4-tetrachloro-7-one-naphthobornadiene.

6. A halogen containing compound of claim 1, wherein said compound is 2,3,4-trichloro-9,10; 4a,9a-tetrahydroanthracene-1-carboxylic acid.

* * * * *